United States Patent
Stephens et al.

(10) Patent No.: US 6,809,236 B1
(45) Date of Patent: Oct. 26, 2004

(54) SOYBEAN VARIETY XB30W03

(75) Inventors: Paul Alan Stephens, Princeton, IL (US); Thomas Charles Corbin, Monticello, IL (US)

(73) Assignee: Pioneer Hi-Bred International Inc., Des Moines, IA (US)

( * ) Notice: Subject to any disclaimer, the term of this patent is extended or adjusted under 35 U.S.C. 154(b) by 91 days.

(21) Appl. No.: 10/355,314

(22) Filed: Jan. 31, 2003

(51) Int. Cl.⁷ .............................. A01H 5/00; A01H 5/10; A01H 1/00; C12N 5/04
(52) U.S. Cl. ........................ 800/312; 800/260; 800/298; 800/295; 435/415; 435/421; 435/426; 435/430; 435/430.1
(58) Field of Search .................................. 800/260, 312, 800/295, 298; 435/415, 421, 426, 430, 430.1

(56) References Cited

U.S. PATENT DOCUMENTS 5,900,526 A * 5/1999 Gebhardt et al. ........... 800/312

OTHER PUBLICATIONS

Plant Variety Protection Certificate No. 9300151 for Soybean A4138, Sep. 30, 1996.

* cited by examiner

*Primary Examiner*—Medina A. Ibrahim
(74) *Attorney, Agent, or Firm*—Pioneer Hi-Bred International, Inc.

(57) ABSTRACT

According to the invention, there is provided a soybean variety designated XB30W03. This invention thus relates to the seeds of soybean variety XB30W03, to the plants of soybean XB30W03 to plant parts of soybean variety XB30W03, and to methods for producing a soybean plant by crossing plants of the soybean variety XB30W03 with another soybean plant, using XB30W03 as either the male or the female parent.

8 Claims, No Drawings

SOYBEAN VARIETY XB30W03

FIELD OF INVENTION

This invention is in the field of soybean breeding, specifically relating to a soybean variety designated XB30W03.

BACKGROUND OF INVENTION

The present invention relates to a new and distinctive soybean variety, designated XB30W03 which has been the result of years of careful breeding and selection as part of a soybean breeding program. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, tolerance to drought and heat, and better agronomic qualities.

These processes, which lead to the final step of marketing and distribution, can take from six to twelve years from the time the first cross is made. Therefore, development of new varieties is a time-consuming process that requires precise forward planning, efficient use of resources, and a minimum of changes in direction.

Soybean (*Glycine max*), is an important and valuable field crop. Thus, a continuing goal of soybean breeders is to develop stable, high yielding soybean varieties that are agronomically sound. The reasons for this goal are obviously to maximize the amount of grain produced on the land used and to supply food for both animals and humans. To accomplish this goal, the soybean breeder must select and develop soybean plants that have the traits that result in superior varieties.

Pioneer soybean research staff creates over 500,000 potential new varieties each year. Of those new varieties, less than 50 and more commonly less than 25 are actually selected for commercial use.

The soybean is the world's leading source of vegetable oil and protein meal. The oil extracted from soybeans is used for cooking oil, margarine, and salad dressings. Soybean oil is composed of saturated, monounsaturated and polyunsaturated fatty acids. It has a typical composition of 11% palmitic, 4% stearic, 25% oleic, 50% linoleic and 9% linolenic fatty acid content ("Economic Implications of Modified Soybean Traits Summary Report", Iowa Soybean Promotion Board & American Soybean Association Special Report 92S, May 1990). Changes in fatty acid composition for improved oxidative stability and nutrition are constantly sought after. Industrial uses of soybean oil which is subjected to further processing include ingredients for paints, plastics, fibers, detergents, cosmetics, and lubricants. Soybean oil may be split, inter-esterified, sulfurized, epoxidized, polymerized, ethoxylated, or cleaved. Designing and producing soybean oil derivatives with improved functionality, oliochemistry, is a rapidly growing field. The typical mixture of triglycerides is usually split and separated into pure fatty acids, which are then combined with petroleum-derived alcohols or acids, nitrogen, sulfonates, chlorine, or with fatty alcohols derived from fats and oils.

Soybean is also used as a food source for both animals and humans. Soybean is widely used as a source of protein for animal feeds for poultry, swine and cattle. During processing of whole soybeans, the fibrous hull is removed and the oil is extracted. The remaining soybean meal is a combination of carbohydrates and approximately 50% protein.

For human consumption soybean meal is made into soybean flour which is processed to protein concentrates used for meat extenders or specialty pet foods. Production of edible protein ingredients from soybean offers a healthy, less expensive replacement for animal protein in meats as well as dairy-type products.

SUMMARY OF INVENTION

According to the invention, there is provided a novel soybean variety, designated XB30W03. This invention thus relates to the seeds of soybean variety XB30W03, to the plants of soybean XB30W03 to plant parts of soybean variety XB30W03 and to methods for producing a soybean plant produced by crossing soybean variety XB30W03 with another soybean plant, using XB30W03 as either the male or the female parent. This invention also relates to methods for producing a soybean plant containing in its genetic material one or more transgenes and to the transgenic soybean plants and plant parts produced by those methods. This invention also relates to soybean varieties or breeding varieties and plant parts derived from soybean variety XB30W03, to methods for producing other soybean varieties, lines or plant parts derived from soybean variety XB30W03 and to the soybean plants, varieties, and their parts derived from use of those methods. This invention further relates to soybean seeds, plants, and plant parts produced by crossing the soybean variety XB30W03 with another soybean variety preferably as part of a breeding program.

Definitions

Certain definitions used in the specification are provided below. Also in the examples which follow, a number of terms are used. In order to provide a clear and consistent understanding of the specification and claims, including the scope to be given such terms, the following definitions are provided:

ALLELE=any of one or more alternative forms of a genetic sequence. In a diploid cell or organism, the two alleles of a given sequence occupy corresponding loci on a pair of homologous chromosomes.

BACKCROSSING=Process in which a breeder crosses a progeny variety back to one of the parental genotypes one or more times.

BREEDING=The genetic manipulation of living organisms.

BU/A=Bushels per Acre. The seed yield in bushels/acre is the actual yield of the grain at harvest.

BSR=Brown Stem Rot Tolerance. This is a visual disease score from 1 to 9 comparing all genotypes in a given test. The score is based on leaf symptoms of yellowing and necrosis caused by brown stem rot. A score of 9 indicates no symptoms. Visual scores range down to a score of 1 which indicates severe symptoms of leaf yellowing and necrosis. In the tables provided herein, susceptible means a score of 1–3 and resistant means a score of 6–9.

CNKR=Stem Canker Tolerance. This is a visual disease score from 1 to 9 comparing all genotypes in a given test. The score is based upon premature plant death. A score of 9 indicates no symptoms, whereas a score of 1 indicates the entire experimental unit died very early.

COTYLEDON=A cotyledon is a type of seed leaf. The cotyledon contains the food storage tissues of the seed.

ELITE VARIETY=A variety that is sufficiently homozygous and homogeneous to be used for commercial grain production. An elite variety may also be used in further breeding.

EMBRYO=The embryo is the small plant contained within a mature seed.

EMGSC=Emergence Score. The percentage of emerged plants in a plot respective to the number of seeds planted.

F3=This symbol denotes a generation resulting from the selfing of the F2 generation along with selection for type and rogueing of off-types. The "F" number is a term commonly used in genetics, and designates the number of the filial generation. The "F3" generation denotes the offspring resulting from the selfing or self mating of members of the generation having the next lower "F" number, viz. the F2 generation.

FEC=Iron-deficiency Chlorosis. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves. Plots are usually scored in mid July.

FECL=Iron-deficiency Chlorosis. Plants are scored 1 to 9 based on visual observations. A score of 1 indicates the plants are dead or dying from iron-deficiency chlorosis, a score of 5 means plants have intermediate health with some leaf yellowing and a score of 9 means no stunting of the plants or yellowing of the leaves. Plots are scored around mid August.

FEY=Frogeye Tolerance. This is a visual disease score from 1 to 9 comparing all genotypes in a given test. The score is based upon leaf lesions. A score of 9 indicates no lesions, whereas a score of 1 indicates severe leaf necrosis.

GIC Count=Seed weight as measured in grams per 100 seeds.

GENOTYPE=Refers to the genetic constitution of a cell or organism.

HABIT=This refers to the physical appearance of a plant. It can be determinate, semi-determinate, intermediate, or indeterminate. In soybeans, indeterminate varieties are those in which stem growth is not limited by formation of a reproductive structure (i.e., flowers, pods and seeds) and hence growth continues throughout flowering and during part of pod filling. The main stem will develop and set pods over a prolonged period under favorable conditions. In soybeans, determinate varieties are those in which stem growth ceases at flowering time. Most flowers develop simultaneously, and most pods fill at approximately the same time. The terms semi-determinate and intermediate are also used to describe plant habit and are defined in Bernard, R. L. 1972. "Two genes affecting stem termination in soybeans." Crop Science 12:235–239; Woodworth, C. M. 1932. "Genetics and breeding in the improvement of the soybean." Bull. Agric. Exp. Stn. (Illinois) 384:297–404; Woodworth, C. M. 1933. "Genetics of the soybean." J. Am. Soc. Agron. 25:36–51.

HGT=Plant Height. Plant height is taken from the top of the soil to top pod of the plant and is measured in inches.

HILUM=This refers to the scar left on the seed which marks the place where the seed was attached to the pod prior to it (the seed) being harvested.

HYPL=Hypocotyl Elongation. This score indicates the ability of the seed to emerge when planted 3" deep in sand pots and with a controlled temperature of 25° C. The number of plants that emerge each day are counted. Based on this data, each genotype is given a 1 to 9 score based on its rate of emergence and percent of emergence. A score of 9 indicates an excellent rate and percent of emergence, an intermediate score of 5 indicates average ratings and a 1 score indicates a very poor rate and percent of emergence.

HYPOCOTYL=A hypocotyl is the portion of an embryo or seedling between the cotyledons and the root. Therefore, it can be considered a transition zone between shoot and root.

LDGSEV=Lodging Resistance. Lodging is rated on a scale of 1 to 9. A score of 9 indicates erect plants. A score of 5 indicates plants are leaning at a 45° angle in relation to the ground and a score of 1 indicates plants are laying on the ground.

LEAFLETS=These are part of the plant shoot, and they manufacture food for the plant by the process of photosynthesis.

LINKAGE=Refers to a phenomenon wherein alleles on the same chromosome tend to segregate together more often than expected by chance if their transmission was independent.

LINKAGE DISEQUILIBRIUM=Refers to a phenomenon wherein alleles tend to remain together in linkage groups when segregating from parents to offspring, with a greater frequency than expected from their individual frequencies.

LLE=Linoleic Acid Percent. Linoleic acid is one of the five most abundant fatty acids in soybean seeds. It is measured by gas chromatography and is reported as a percent of the total oil content.

LLN=Linolenic Acid Percent. Linolenic acid is one of the five most abundant fatty acids in soybean seeds. It is measured by gas chromatography and is reported as a percent of the total oil content.

MAT ABS=Absolute Maturity. This term is defined as the length of time from planting to complete physiological development (maturity). The period from planting until maturity is reached is measured in days, usually in comparison to one or more standard varieties. Plants are considered mature when 95% of the pods have reached their mature color.

MATURITY GROUP=This refers to an agreed-on industry division of groups of varieties, based on the zones in which they are adapted primarily according to day length or latitude. They consist of very long day length varieties (Groups 000, 00, 0), and extend to very short day length varieties (Groups VII, VII, IX, X).

OIL=Oil Percent. Soybean seeds contain a considerable amount of oil. Oil is measured by NIR spectrophotometry, and is reported on an as is percentage basis.

OLC=Oleic Acid Percent. Oleic acid is one of the five most abundant fatty acids in soybean seeds. It is measured by gas chromatography and is reported as a percent of the total oil content.

PEDIGREE DISTANCE=Relationship among generations based on their ancestral links as evidenced in pedigrees. May be measured by the distance of the pedigree from a given starting point in the ancestry.

PRT=Phytophthora megasperma var sojae response. PRT or PRTLAB is a visual disease score from 1 to 9 comparing all genotypes in a given test, including known resistant and susceptible checks for use as references in scoring. The score is based upon assessing soybean seedlings for damage from hypocotyl inoculation with a race specific culture. A score of 9 indicates that the seedling is as viable as the resistant check, and a score of 1 indicates that the seedling is as damaged as the susceptible check. In the tables provided herein, susceptible means a score of 1–3 and resistant means a score of 6–9. When response is shown with reference to a particular phytophthora race (PMG), such response is determined by a specific allele conferring race specific resistance. Individual alleles as individual loci can be determined by marker analysis and/or bioassay.

PLM=Palmitic Acid Percent. Palmitic acid is one of the five most abundant fatty acids in soybean seeds. It is measured by gas chromatography and is reported as a percent of the total oil content.

POD=This refers to the fruit of a soybean plant. It consists of the hull or shell (pericarp) and the soybean seeds.

PRMMAT=Predicted Relative Maturity. Soybean maturities are divided into relative maturity groups. In the United States the most common maturity groups are 00 through VIII. Within maturity groups 00 through V are sub-groups. A sub-group is a tenth of a relative maturity group. Within narrow comparisons, the difference of a tenth of a relative maturity group equates very roughly to a day difference in maturity at harvest.

PRO=Protein Percent. Soybean seeds contain a considerable amount of protein. Protein is generally measured by NIR spectrophotometry, and is reported on an as is percentage basis.

PUBESCENCE=This refers to a covering of very fine hairs closely arranged on the leaves, stems and pods of the soybean plant.

RKI=Root-knot Nematode, Southern. This is a visual disease score from 1 to 9 comparing all genotypes in a given test. The score is based upon digging plants to visually score the roots for presence or absence of galling. A score of 9 indicates that there is no galling of the roots, a score of 1 indicates large severe galling cover most of the root system which results in pre-mature death from decomposing of the root system.

RKA=Root-knot Nematode, Peanut. This is a visual disease score from 1to 9 comparing all genotypes in a given test. The score is based upon digging plants to look at the roots for presence or absence of galling. A score of 9 indicates that there is no galling of the roots, a score of 1 indicates large severe galling cover most of the root system which results in pre-mature death from decomposing of the root system.

SCN=Soybean Cyst Nematode Response. This is a visual disease score from 1 to 9 comparing all genotypes in a given test, including known resistant and susceptible checks for use as references in scoring. The score is based upon assessing soybean seedling roots for the number of cysts. A score of 9 indicates that the number of cysts on the roots of the experimental variety is equal to or less than 7% of the number of cysts on the roots of the susceptible check, and a score of 1 indicates that the number of cysts on the roots of the experimental variety is equal to or greater than the number of cysts on the roots of the susceptible check. In the tables provided herein, susceptible means a score of 1–3 and resistant means a score of 6–9.

SD VIG=Seedling Vigor. The score is based on the speed of emergence of the plants within a plot relative to other plots within an experiment. A score of 9 indicates that 90% of plants growing have expanded first leaves. A score of 1 indicates no plants have expanded first leaves.

SDS=Sudden Death Syndrome. Tolerance to Sudden Death Syndrome is rated on a scale of 1 to 9, with a score of 1 being very susceptible ranging up to a score of 9 being tolerant.

S/LB=Seeds per Pound. Soybean seeds vary in seed size, therefore, the number of seeds required to make up one pound also varies. This affects the pounds of seed required to plant a given area, and can also impact end uses.

SHATTR=Shattering. This refers to the amount of pod dehiscence prior to harvest. Pod dehiscence involves seeds falling from the pods to the soil. This is a visual score from 1 to 9 comparing all genotypes within a given test. A score of 9 means pods have not opened and no seeds have fallen out. A score of 5 indicates approximately 50% of the pods have opened, with seeds falling to the ground and a score of 1 indicates 100% of the pods are opened.

SHOOTS=These are a portion of the body of the plant. They consist of stems, petioles and leaves.

STC=Stearic Acid Percent. Stearic acid is one of the five most abundant fatty acids in soybean seeds. It is measured by gas chromatography and is reported as a percent of the total oil content.

WH MD=White Mold Tolerance. This is a visual disease score from 1 to 9 comparing all genotypes in a given test. The score is based upon observations of mycelial growth and death of plants. A score of 9 indicates no symptoms. Visual scores of 1 indicate complete death of the experimental unit.

YIELD BU/A=Yield (Bushels/Acre). Yield of the grain at harvest in bushels per acre adjusted to 13.5% moisture, with a bushel being equal to 60 pounds.

Definitions for Area of Adaptability

When referring to area of adaptability, such term is used to describe the location with the environmental conditions that would be well suited for this soybean variety. Area of adaptability is based on a number of factors, for example: days to maturity, insect resistance, disease resistance, and drought resistance. Area of adaptability does not indicate that the soybean variety will grow in every location within the area of adaptability or that it will not grow outside the area.

Midwest: Iowa and Missouri
Heartland: Illinois and the western half of Indiana
Plains: ⅔ of the eastern parts of South Dakota and Nebraska
North Central: Minnesota, Wisconsin, the Upper Peninsula of Michigan, and the eastern half of North Dakota
Mideast: Michigan, Ohio, and the eastern half of Indiana
Eastern: Pennsylvania, Delaware, Maryland, Rhode Island, New Jersey, Connecticut, Massachusetts, New York, Vermont, and Maine
Southern: Virginia, West Virginia, Tennessee, Kentucky, Arkansas, North Carolina, South Carolina, Georgia, Florida, Alabama, Mississippi, and Louisiana
Western: Texas, Kansas, Colorado, Oklahoma, New Mexico, Arizona, Utah, Nevada, California, Washington, Oregon, Montana, Idaho, Wyoming, the western half of North Dakota, and the western ⅓ South Dakota and Nebraska
PMG infested soils: soils containing *Phytophthora megasperma*
Narrow rows: 7" and 15" row spacing
High yield environments: areas which lack normal stress for example they have sufficient rainfall, water drainage, low disease pressure, and low weed pressure Tough environments: areas which have stress challenges, opposite of a high yield environment

DETAILED DESCRIPTION OF INVENTION

The variety of the invention has shown uniformity and stability for all traits, as described in the following variety description information. It has been self-pollinated a sufficient number of generations, with careful attention to uniformity of plant type to ensure homozygosity and phenotypic stability. The variety has been increased with continued observation for uniformity. No variant traits have been observed or are expected in XB30W03, as described in Table 1 (Variety Description Information).

Soybean variety XB30W03 is a purple flowered soybean variety with light tawny colored plant pubescence and black colored hila. Soybean variety XB30W03 is in the relative maturity group 3, sub-group 0, and is particularly adapted to the Plains, Western, Mideast, Midwest, Heartland and Eastern areas of the United States. This variety does well in Soybean Cyst Nematode infected soils. The variety XB30W03 demonstrates a good tolerance to Brown Stem Rot and to sudden death syndrome. This variety displays a substantial degree of glyphosate resistance.

Soybean variety XB30W03, being substantially homozygous, can be reproduced by planting seeds of the variety, growing the resulting soybean plants under self-pollinating or sib-pollinating conditions, and harvesting the resulting seed, using techniques familiar to the agricultural arts.

TABLE 1

Variety Description Information
XB30W03

| | |
|---|---|
| A. | Mature Seed Characteristics: |
| | Seed Coat Color: yellow |
| | Seed Size (grams per 100 seeds): 14 |
| | Hilum Color: black |
| | Seed Shape: spherical-flattened |
| | Seed Coat Luster: dull |
| B. | Leaf: |
| | Leaflet Shape: ovate |
| C. | Plant Characteristics: |
| | Flower Color: purple |
| | Pod Color: tan |
| | Cotyledon Color: yellow |
| | Hypocotyl Color: light purple |
| | Plant Pubescence Color: light tawny |
| | Plant Habit: indeterminate |
| | Maturity Group: 3 |
| | Maturity SubGroup: 0 |

TABLE 1-continued

Variety Description Information
XB30W03

| | |
|---|---|
| D. | Fungal Diseases (S = susceptible R = resistant) |
| | Phytophthora Root Rot |
| | Race 3: S |
| | Race 7: S |
| | Race 25: S |
| | Brown Stem Rot: R |
| E. | Nematode Diseases (S = susceptible R = resistant) |
| | Soybean Cyst Nematode |
| | Race 3: R |
| F. | Glyphosate: Resistant |

Publications useful as references in interpreting Table1 include:

Caldwell, B. E. ed. 1973."Soybeans: Improvement, Production, and Uses" Amer. Soc. Agron. Monograph No. 16;

Buttery, B. R., and R. I. Buzzell 1968. "Peroxidase Activity in Seed of Soybean Varieties" Crop Sci. 8: 722–725;

Hymowitz, T. 1973. "Electrophoretic analysis of SBTI-A2 in the USDA Soybean Germplasm Collection" Crop Sci., 13: 420–421;

Payne R. C., and L. F. Morris, 1976. "Differentiation of Soybean Varieties by Seedling Pigmentation Patterns" J. Seed. Technol. 1: 1–19. The disclosures of which are each incorporated by reference in their entirety.

Performance Examples of XB30W03

In the examples that follow in Table 2, the traits and characteristics of soybean variety XB30W03 given in paired comparisons with the eight Pioneer varieties 92B92 (Table 2A), 93B01 (Table 2B), 93B09 (Table 2C), 93B26 (Table 2D), 93B35 (Table 2E), 93B36 (Table 2F), 93B47 (Table 2G) and 93B53 (Table 2H).

TABLE 2A

VARIETY COMPARISON
DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 92B95 | Mean1 | 52.5 | 129.6 | 7 | 36 |
| XB30W03 | 92B95 | Mean2 | 44.7 | 127.1 | 6.5 | 33 |
| XB30W03 | 92B95 | #Locs | 47 | 17 | 11 | 18 |
| XB30W03 | 92B95 | #Reps | 69 | 22 | 16 | 23 |
| XB30W03 | 92B95 | #Years | 2 | 2 | 2 | 2 |
| XB30W03 | 92B95 | Diff | 7.8 | 2.6 | 0.5 | −4 |
| XB30W03 | 92B95 | Prob | 0 | 0.0001 | 0.111 | 0.0002 |

| Variety1 | Variety2 | Statistic | FEC score ABS | SDS score ABS | PRTLAB score ABS | EMGSC score ABS |
|---|---|---|---|---|---|---|
| XB30W03 | 92B95 | Mean1 | 5.2 | 8.5 | 5.6 | 7.2 |
| XB30W03 | 92B95 | Mean2 | 4.5 | 8.2 | 4.9 | 7.5 |
| XB30W03 | 92B95 | #Locs | 2 | 4 | 2 | 2 |
| XB30W03 | 92B95 | #Reps | 6 | 10 | 5 | 6 |
| XB30W03 | 92B95 | #Years | 1 | 2 | 2 | 2 |
| XB30W03 | 92B95 | Diff | 0.7 | 0.4 | 0.7 | −0.3 |
| XB30W03 | 92B95 | Prob | 0.2952 | 0.391 | 0.7048 | 1 |

TABLE 2A-continued

VARIETY COMPARISON DATA FOR XB30W03

| Variety1 | Variety2 | Statistic | SDVIG score ABS | OILT pct ABS | PROT pct ABS | G/C count ABS |
|---|---|---|---|---|---|---|
| XB30W03 | 92B95 | Mean1 | 7.3 | 22.4 | 39.6 | 16.1 |
| XB30W03 | 92B95 | Mean2 | 6.5 | 21.8 | 39.7 | 13.9 |
| XB30W03 | 92B95 | #Locs | 2 | 9 | 9 | 9 |
| XB30W03 | 92B95 | #Reps | 6 | 9 | 9 | 9 |
| XB30W03 | 92B95 | #Years | 2 | 2 | 2 | 2 |
| XB30W03 | 92B95 | Diff | 0.8 | 0.5 | −0.1 | 2.3 |
| XB30W03 | 92B95 | Prob | 0.1257 | 0.0152 | 0.8148 | 0.0034 |

TABLE 2B

VARIETY COMPARISON DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B01 | Mean1 | 52.5 | 130.1 | 7 | 36 |
| XB30W03 | 93B01 | Mean2 | 50 | 127.1 | 8.6 | 31 |
| XB30W03 | 93B01 | #Locs | 52 | 19 | 11 | 18 |
| XB30W03 | 93B01 | #Reps | 74 | 24 | 16 | 23 |
| XB30W03 | 93B01 | #Years | 3 | 3 | 2 | 2 |
| XB30W03 | 93B01 | Diff | 2.5 | 3 | −1.6 | −6 |
| XB30W03 | 93B01 | Prob | 0.0068 | 0 | 0.0028 | 0 |

| Variety1 | Variety2 | Statistic | FEC score ABS | SDS score ABS | PRTLAB score ABS | EMGSC score ABS |
|---|---|---|---|---|---|---|
| XB30W03 | 93B01 | Mean1 | 5.2 | 8.5 | 5.6 | 7.2 |
| XB30W03 | 93B01 | Mean2 | 5.3 | 6.9 | 6.3 | 7.7 |
| XB30W03 | 93B01 | #Locs | 2 | 4 | 2 | 2 |
| XB30W03 | 93B01 | #Reps | 6 | 10 | 5 | 6 |
| XB30W03 | 93B01 | #Years | 1 | 2 | 2 | 2 |
| XB30W03 | 93B01 | Diff | −0.2 | 1.6 | −0.7 | −0.5 |
| XB30W03 | 93B01 | Prob | 0.8743 | 0.1982 | 0.7578 | 0.5 |

| Variety1 | Variety2 | Statistic | SDVIG score ABS | OILT pct ABS | PROT pct ABS | G/C count ABS |
|---|---|---|---|---|---|---|
| XB30W03 | 93B01 | Mean1 | 7.3 | 22.3 | 39.9 | 16.1 |
| XB30W03 | 93B01 | Mean2 | 7.3 | 23.2 | 39.8 | 12.9 |
| XB30W03 | 93B01 | #Locs | 2 | 8 | 8 | 9 |
| XB30W03 | 93B01 | #Reps | 6 | 8 | 8 | 9 |
| XB30W03 | 93B01 | #Years | 2 | 2 | 2 | 2 |
| XB30W03 | 93B01 | Diff | 0 | −0.9 | 0.1 | 3.3 |
| XB30W03 | 93B01 | Prob | 1 | 0.0014 | 0.8522 | 0 |

TABLE 2C

VARIETY COMPARISON DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B09 | Mean1 | 54.2 | 127.3 | 7.4 | 35 |
| XB30W03 | 93B09 | Mean2 | 54.2 | 126.9 | 8.3 | 32 |
| XB30W03 | 93B09 | #Locs | 26 | 9 | 6 | 8 |
| XB30W03 | 93B09 | #Reps | 47 | 14 | 11 | 13 |
| XB30W03 | 93B09 | #Years | 1 | 1 | 1 | 1 |
| XB30W03 | 93B09 | Diff | 0 | 0.4 | −0.9 | −3 |
| XB30W03 | 93B09 | Prob | 0.9689 | 0.5563 | 0.006 | 0.0067 |

TABLE 2C-continued

VARIETY COMPARISON
DATA FOR XB30W03

| Variety1 | Variety2 | Statistic | FEC score ABS | SDS score ABS | PRTLAB score ABS | EMGSC score ABS |
|---|---|---|---|---|---|---|
| XB30W03 | 93B09 | Mean1 | 5.2 | 8.4 | 4.7 | 6.7 |
| XB30W03 | 93B09 | Mean2 | 5.8 | 7.6 | 6 | 7.3 |
| XB30W03 | 93B09 | #Locs | 2 | 3 | 1 | 1 |
| XB30W03 | 93B09 | #Reps | 6 | 7 | 3 | 3 |
| XB30W03 | 93B09 | #Years | 1 | 1 | 1 | 1 |
| XB30W03 | 93B09 | Diff | −0.7 | 0.8 | −1.3 | −0.7 |
| XB30W03 | 93B09 | Prob | 0.2952 | 0.3356 | | |

| Variety1 | Variety2 | Statistic | SDVIG score ABS | OILT pct ABS | PROT pct ABS | G/C count ABS |
|---|---|---|---|---|---|---|
| XB30W03 | 93B09 | Mean1 | 8.3 | 22.7 | 40.1 | 16.5 |
| XB30W03 | 93B09 | Mean2 | 8 | 24.5 | 39.8 | 16.7 |
| XB30W03 | 93B09 | #Locs | 1 | 5 | 5 | 5 |
| XB30W03 | 93B09 | #Reps | 3 | 5 | 5 | 5 |
| XB30W03 | 93B09 | #Years | 1 | 1 | 1 | 1 |
| XB30W03 | 93B09 | Diff | 0.3 | −1.8 | 0.3 | −0.2 |
| XB30W03 | 93B09 | Prob | | 0.0011 | 0.7111 | 0.6284 |

TABLE 2D

VARIETY COMPARISON
DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B26 | Mean1 | 52.5 | 130.1 | 7 | 36 |
| XB30W03 | 93B26 | Mean2 | 45.4 | 131.4 | 6 | 35 |
| XB30W03 | 93B26 | #Locs | 52 | 19 | 11 | 18 |
| XB30W03 | 93B26 | #Reps | 74 | 24 | 16 | 23 |
| XB30W03 | 93B26 | #Years | 3 | 3 | 2 | 2 |
| XB30W03 | 93B26 | Diff | 7 | −1.3 | 1 | −2 |
| XB30W03 | 93B26 | Prob | 0 | 0.01 | 0.043 | 0.0445 |

| Variety1 | Variety2 | Statistic | FEC score ABS | SDS score ABS | PRTLAB score ABS | EMGSC score ABS |
|---|---|---|---|---|---|---|
| XB30W03 | 93B26 | Mean1 | 5.2 | 8.5 | 5.6 | 7.2 |
| XB30W03 | 93B26 | Mean2 | 4.3 | 7.8 | 5.7 | 7.8 |
| XB30W03 | 93B26 | #Locs | 2 | 4 | 2 | 2 |
| XB30W03 | 93B26 | #Reps | 6 | 10 | 5 | 6 |
| XB30W03 | 93B26 | #Years | 1 | 2 | 2 | 2 |
| XB30W03 | 93B26 | Diff | 0.8 | 0.8 | −0.1 | −0.7 |
| XB30W03 | 93B26 | Prob | 0.6051 | 0.0182 | 0.9097 | 1 |

| Variety1 | Variety2 | Statistic | SDVIG score ABS | OILT pct ABS | PROT pct ABS | G/C count ABS |
|---|---|---|---|---|---|---|
| XB30W03 | 93B26 | Mean1 | 7.3 | 22.4 | 39.6 | 16.1 |
| XB30W03 | 93B26 | Mean2 | 7.3 | 22.2 | 39.3 | 13.4 |
| XB30W03 | 93B26 | #Locs | 2 | 9 | 9 | 9 |
| XB30W03 | 93B26 | #Reps | 6 | 9 | 9 | 9 |
| XB30W03 | 93B26 | #Years | 2 | 2 | 2 | 2 |
| XB30W03 | 93B26 | Diff | 0 | 0.2 | 0.3 | 2.8 |
| XB30W03 | 93B26 | Prob | 1 | 0.3167 | 0.3261 | 0 |

TABLE 2E

VARIETY COMPARISON DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B35 | Mean1 | 53.7 | 128.5 | 7.4 | 35 |
| XB30W03 | 93B35 | Mean2 | 49.6 | 131 | 8.4 | 29 |
| XB30W03 | 93B35 | #Locs | 31 | 11 | 6 | 8 |
| XB30W03 | 93B35 | #Reps | 53 | 16 | 11 | 13 |
| XB30W03 | 93B35 | #Years | 2 | 2 | 1 | 1 |
| XB30W03 | 93B35 | Diff | 4.1 | −2.4 | −1 | −6 |
| XB30W03 | 93B35 | Prob | 0.0008 | 0.0037 | 0.0006 | 0.0001 |

| Variety1 | Variety2 | Statistic | FEC score ABS | SDS score ABS | PRTLAB score ABS | EMGSC score ABS |
|---|---|---|---|---|---|---|
| XB30W03 | 93B35 | Mean1 | 5.2 | 8.4 | 4.7 | 6.7 |
| XB30W03 | 93B35 | Mean2 | 4.2 | 5.5 | 6.3 | 8 |
| XB30W03 | 93B35 | #Locs | 2 | 3 | 1 | 1 |
| XB30W03 | 93B35 | #Reps | 6 | 7 | 3 | 3 |
| XB30W03 | 93B35 | #Years | 1 | 1 | 1 | 1 |
| XB30W03 | 93B35 | Diff | 1 | 2.9 | −1.7 | −1.3 |
| XB30W03 | 93B35 | Prob | 0.5 | 0.1576 | | |

| Variety1 | Variety2 | Statistic | SDVIG score ABS | OILT pct ABS | PROT pct ABS | G/C count ABS |
|---|---|---|---|---|---|---|
| XB30W03 | 93B35 | Mean1 | 8.3 | 22.7 | 40.1 | 16.5 |
| XB30W03 | 93B35 | Mean2 | 8 | 23.2 | 40.8 | 14.9 |
| XB30W03 | 93B35 | #Locs | 1 | 5 | 5 | 5 |
| XB30W03 | 93B35 | #Reps | 3 | 5 | 5 | 5 |
| XB30W03 | 93B35 | #Years | 1 | 1 | 1 | 1 |
| XB30W03 | 93B35 | Diff | 0.3 | −0.6 | −0.8 | 1.7 |
| XB30W03 | 93B35 | Prob | | 0.0129 | 0.2254 | 0.0013 |

TABLE 2F

VARIETY COMPARISON DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B36 | Mean1 | 54.2 | 127.3 | 7.4 | 35 |
| XB30W03 | 93B36 | Mean2 | 55.3 | 129.4 | 8.3 | 33 |
| XB30W03 | 93B36 | #Locs | 26 | 9 | 6 | 8 |
| XB30W03 | 93B36 | #Reps | 47 | 14 | 11 | 13 |
| XB30W03 | 93B36 | #Years | 1 | 1 | 1 | 1 |
| XB30W03 | 93B36 | Diff | −1.1 | −2.1 | −0.8 | −2 |
| XB30W03 | 93B36 | Prob | 0.273 | 0.0556 | 0.0305 | 0.0457 |

| Variety1 | Variety2 | Statistic | FEC score ABS | SDS score ABS | PRTLAB score ABS | EMGSC score ABS |
|---|---|---|---|---|---|---|
| XB30W03 | 93B36 | Mean1 | 5.2 | 8.4 | 4.7 | 6.7 |
| XB30W03 | 93B36 | Mean2 | 4.8 | 7.2 | 6 | 8 |
| XB30W03 | 93B36 | #Locs | 2 | 3 | 1 | 1 |
| XB30W03 | 93B36 | #Reps | 6 | 7 | 3 | 3 |
| XB30W03 | 93B36 | #Years | 1 | 1 | 1 | 1 |
| XB30W03 | 93B36 | Diff | 0.3 | 1.2 | −1.3 | −1.3 |
| XB30W03 | 93B36 | Prob | 0.5 | 0.3112 | | |

| Variety1 | Variety2 | Statistic | SDVIG score ABS | OILT pct ABS | PROT pct ABS | G/C count ABS |
|---|---|---|---|---|---|---|
| XB30W03 | 93B36 | Mean1 | 8.3 | 22.7 | 40.1 | 16.5 |
| XB30W03 | 93B36 | Mean2 | 7.3 | 22.3 | 41.5 | 16.1 |
| XB30W03 | 93B36 | #Locs | 1 | 5 | 5 | 5 |
| XB30W03 | 93B36 | #Reps | 3 | 5 | 5 | 5 |
| XB30W03 | 93B36 | #Years | 1 | 1 | 1 | 1 |
| XB30W03 | 93B36 | Diff | 1 | 0.3 | −1.4 | 0.4 |
| XB30W03 | 93B36 | Prob | 0.1354 | 0.0967 | 0.3512 | |

TABLE 2G

VARIETY COMPARISON DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B47 | Mean1 | 54.2 | 127.3 | 7.4 | 35 |
| XB30W03 | 93B47 | Mean2 | 53.4 | 130.9 | 7.5 | 35 |
| XB30W03 | 93B47 | #Locs | 26 | 9 | 6 | 8 |
| XB30W03 | 93B47 | #Reps | 48 | 14 | 11 | 13 |
| XB30W03 | 93B47 | #Years | 1 | 1 | 1 | 1 |
| XB30W03 | 93B47 | Diff | 0.8 | −3.6 | −0.1 | 0 |
| XB30W03 | 93B47 | Prob | 0.4164 | 0.0011 | 0.7926 | 0.7358 |

| Variety1 | Variety2 | Statistic | FEC score ABS | SDS score ABS | PRTLAB score ABS | EMGSC score ABS |
|---|---|---|---|---|---|---|
| XB30W03 | 93B47 | Mean1 | 5.2 | 8.4 | 4.7 | 6.7 |
| XB30W03 | 93847 | Mean2 | 4.7 | 6.4 | 5.3 | 8.3 |
| XB30W03 | 93B47 | #Locs | 2 | 3 | 1 | 1 |
| XB30W03 | 93B47 | #Reps | 6 | 7 | 3 | 3 |
| XB30W03 | 93B47 | #Years | 1 | 1 | 1 | 1 |
| XB30W03 | 93B47 | Diff | 0.5 | 2 | −0.7 | −1.7 |
| XB30W03 | 93B47 | Prob | 0.656 | 0.1201 | | |

| Variety1 | Variety2 | Statistic | SDVIG score ABS | OILT pct ABS | PROT pct ABS | G/C count ABS |
|---|---|---|---|---|---|---|
| XB30W03 | 93B47 | Mean1 | 8.3 | 22.7 | 40.1 | 16.5 |
| XB30W03 | 93B47 | Mean2 | 9 | 22.7 | 40.7 | 15.9 |
| XB30W03 | 93B47 | #Locs | 1 | 5 | 5 | 5 |
| XB30W03 | 93B47 | #Reps | 3 | 5 | 5 | 5 |
| XB30W03 | 93B47 | #Years | 1 | 1 | 1 | 1 |
| XB30W03 | 93B47 | Diff | −0.7 | −0.1 | −0.7 | 0.6 |
| XB30W03 | 93B47 | Prob | | 0.7857 | 0.1302 | 0.0474 |

TABLE 2H

VARIETY COMPARISON DATA FOR XB30W03

| Variety1 | Variety2 | Statistic | YIELD bu/a 60# ABS | MATABS count ABS | LDGSEV score ABS | HGT in ABS |
|---|---|---|---|---|---|---|
| XB30W03 | 93B53 | Mean1 | 54.2 | 127.3 | 7.4 | 35 |
| XB30W03 | 93B53 | Mean2 | 51.1 | 130.3 | 8.5 | 33 |
| XB30W03 | 93B53 | #Locs | 26 | 9 | 6 | 8 |
| XB30W03 | 93B53 | #Reps | 48 | 14 | 11 | 13 |
| XB30W03 | 93B53 | #Years | 1 | 1 | 1 | 1 |
| XB30W03 | 93B53 | Diff | 3.1 | −2.9 | −1.1 | −3 |
| XB30W03 | 93B53 | Prob | 0.0059 | 0.0099 | 0.0062 | 0.0358 |

| Variety1 | Variety2 | Statistic | FEC score ABS | SDS score ABS | PRTLAB score ABS | EMGSC score ABS |
|---|---|---|---|---|---|---|
| XB30W03 | 93B53 | Mean1 | 5.2 | 8.4 | 4.7 | 6.7 |
| XB30W03 | 93B53 | Mean2 | 5.5 | 6.2 | 6.7 | 7.3 |
| XB30W03 | 93B53 | #Locs | 2 | 3 | 1 | 1 |
| XB30W03 | 93B53 | #Reps | 6 | 7 | 3 | 3 |
| XB30W03 | 93B53 | #Years | 1 | 1 | 1 | 1 |
| XB30W03 | 93B53 | Diff | −0.3 | 2.2 | −2 | −0.7 |
| XB30W03 | 93B53 | Prob | 0.5 | 0.2675 | | |

| Variety1 | Variety2 | Statistic | SDVIG score ABS | OILT pct ABS | PROT pct ABS | G/C count ABS |
|---|---|---|---|---|---|---|
| XB30W03 | 93B53 | Mean1 | 8.3 | 22.7 | 40.1 | 16.5 |
| XB30W03 | 93B53 | Mean2 | 7.7 | 23.2 | 39.7 | 15 |
| XB30W03 | 93B53 | #Locs | 1 | 5 | 5 | 5 |
| XB30W03 | 93B53 | #Reps | 3 | 5 | 5 | 5 |
| XB30W03 | 93B53 | #Years | 1 | 1 | 1 | 1 |
| XB30W03 | 93B53 | Diff | 0.7 | −0.5 | 0.4 | 1.6 |
| XB30W03 | 93B53 | Prob | | 0.0956 | 0.454 | 0.0007 |

Genetic Marker Profile Through SSR

The present invention also comprises a soybean plant which may be characterized by molecular and physiological data obtained from the representative sample of said variety deposited with the ATCC. Further provided by the invention is a soybean plant formed by the combination of the disclosed soybean plant or plant cell with another soybean plant or cell and characterized by being heterozygous for the molecular data of the variety.

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" Crop Science 39:1464–1490 (1999), which is incorporated by reference herein in its entirety.

Particular markers used for these purposes are not limited to any particular set of markers, but are envisioned to include any type of marker and marker profile which provides a means of distinguishing varieties. One method of comparison is where only the loci for which XB30W03 is homozygous are used. For example, one set of publicly available markers which could be used to screen and identify variety XB30W03 is disclosed in Table 3.

TABLE 3

Soybean SSR Marker Set

| Marker | | |
|---|---|---|
| | Sctt008 | |
| | Satt328 | Satt495 |
| Satt572 | Satt372 | Satt523 |
| Satt165 | Satt582 | Satt284 |
| Satt042 | Satt389 | Satt513 |
| Satt300 | Satt543 | |
| Satt050 | Satt186 | Satt590 |
| Satt385 | Sct137 | Satt150 |
| Satt545 | | Satt567 |
| Satt225 | Satt213 | Satt540 |
| Satt133 | Satt384 | Satt175 |
| | Satt411 | Satt551 |
| Satt233 | Satt598 | Satt250 |
| Satt327 | Satt204 | Satt336 |
| Satt421 | Satt602 | |
| Satt470 | Satt452 | Satt255 |
| Satt455 | | Satt234 |
| Satt409 | Satt193 | Satt257 |
| Satt228 | Satt348 | |
| | Sct188 | Satt358 |
| Satt426 | Satt144 | Satt259 |
| Satt509 | Sat090 | Satt420 |
| Satt251 | | Satt262 |
| Satt197 | Satt594 | Satt478 |
| | Satt303 | Satt592 |
| Satt577 | Satt517 | Satt153 |
| Satt467 | Sat117 | Satt243 |
| Sct034 | Sct187 | |
| Satt304 | | |
| Satt601 | Satt353 | |
| Satt556 | Satt568 | |

TABLE 3-continued

Soybean SSR Marker Set

| | | |
|---|---|---|
| Satt122 | Sctt009 | |
| Satt534 | Satt279 | |
| | Satt142 | |
| Satt565 | | |
| Sct186 | | |
| | Satt451 | |
| Satt227 | Satt367 | |
| Satt432 | Satt127 | |
| Satt457 | Sctt012 | |
| Satt557 | Satt270 | |
| Sct028 | Sat104 | |
| Satt357 | Satt440 | |
| Satt532 | Satt249 | |
| Satt221 | Sct046 | |
| Satt383 | Satt596 | |
| Satt295 | Satt380 | |
| Satt507 | Satt183 | |
| Satt147 | Satt431 | |
| Satt216 | Satt102 | |
| Satt266 | Satt555 | |
| Satt412 | Satt441 | |
| Satt546 | Satt475 | |
| Satt172 | Satt196 | |

Primers and PCR protocols for assaying these markers are disclosed at the world wide web 129.186.26.94/SSR.html. In addition to being used for identification of soybean variety XB30W03, a soybean plant produced through the use of XB30W03, and the identification or verification of pedigree for progeny plants produced through the use of XB30W03, the genetic marker profile is also useful in breeding and developing backcross conversions.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR™ detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by gel electrophoresis of the amplification products. Scoring of marker genotype is based on the size of the amplified fragment as measured by molecular weight (MW) rounded to the nearest integer. While variation in the primer used or in laboratory procedures can affect the reported molecular weight, relative values should remain constant regardless of the specific primer or laboratory used. When comparing varieties it is preferable if all SSR profiles are performed in the same lab.

Primers used are publicly available and may be found in the Soybase supra. or Cregan supra. See also, PCT Publication No. WO 99/31964 Nucleotide Polymorphisms in Soybean, U.S. Pat. No. 6,162,967 Positional Cloning of Soybean Cyst Nematode Resistance Genes, and US2002/0129402A1 Soybean Sudden Death Syndrome Resistant Soybeans and Methods of Breeding and Identifying Resistant Plants, the disclosure of which are incorporated herein by reference.

The SSR profile of soybean plant XB30W03 can be used to identify plants comprising XB30W03 as a parent, since such plants will comprise the same alleles as XB30W03. Because the soybean variety is essentially homozygous at all relevant loci, an inbred should, in almost all cases, have only one allele at each locus. In contrast, a genetic marker profile of an F1 progeny should be the sum of those parents, e.g., if one parent had the allele 112 (base pairs) at a particular locus, and the other parent had 198 the F1 progeny is 112.198 (heterozygous) by inference. Subsequent generations of progeny produced by selection and breeding are expected to be of genotype 112 (homozygous), 198 (homozygous), or 112.198 for that locus position. When the F1 plant is selfed or sibbed for successive filial generations, the locus should be either 112 or 198 for that position.

In addition, plants and plant parts substantially benefiting from the use of XB30W03 in their development such as XB30W03 comprising a backcross conversion, transgene, or genetic sterility factor, may be identified by having a molecular marker profile with a high percent identity to XB30W03. Such a percent identity might be 95%, 96%, 97%, 98%, 99%, 99.5% or 99.9% identical to XB30WO3.

The SSR profile of XB30W03 also can be used to identify essentially derived varieties and other progeny varieties developed from the use of XB30W03, as well as cells and other plant parts thereof. Progeny plants and plant parts produced using XB30W03 may be identified by having a molecular marker profile of at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from soybean variety. Such plants may be developed using the markers identified in WO 00/31964, U.S. Pat. No. 6,162,967 and US2002/0129402A1.

Unique SSR Profiles

While determining the SSR genetic marker profile of the plants described supra, several unique SSR profiles may be identified which did not appear in either parent of such plant. Such unique SSR profiles may arise during the breeding process from recombination or mutation. A combination of several unique alleles provides a means of identifying a plant variety, an F1 progeny produced from such variety, and progeny produced from such variety. Such progeny may be further characterized as being within a pedigree distance of XB30W03, such as within 1,2,3,4 or 5 or less cross-pollinations to a soybean plant other than XB30W03 or a plant that has XB30W03 as a progenitor. Unique molecular profiles may be identified with other molecular tools such as SNPs and RFLPs.

The goal of soybean breeding is to develop new, unique and superior soybean varieties. In practical application of a chosen soybean breeding program, the breeder initially selects and crosses two or more parental varieties, followed by repeated selfing and selection, producing many new genetic combinations. Once a particular variety is used in a soybean program, each resultant cross thereafter will retain the benefit of the use of the initial parent. Each and every cross made from a variety XB30W03 provides benefit to the breeder resulting from the unique combination of alleles present in variety XB30W03 that are not present in any other plant. Soybean variety XB30W03 was selected not only for its own beneficial agronomic traits but also for its favorable breeding characteristics. Use of XB30W03 as a source of breeding material confers benefit far beyond an initial cross and provides a benefit to an entire breeding program which uses XB30W03 as a source of germplasm. Two breeders will never develop the same variety, or even very similar varieties, having the same soybean traits and the use of variety XB30W03 in a breeding program provides benefits from the favorable combination of not just agronomic traits but also traits which confer a breeding advantage.

Each year, the plant breeder selects the germplasm to advance to the next generation. This germplasm is grown under unique and different geographical, climatic and soil conditions, and further selections are then made during and at the end of the growing season.

Proper testing should detect major faults and establish the level of superiority or improvement over current varieties. In addition to showing superior performance, there must be a demand for a new variety. The new variety must be compatible with industry standards, or must create a new market. The introduction of a new variety may incur additional costs to the seed producer, the grower, processor and consumer, for special advertising and marketing, altered seed and commercial production practices, and new product utilization. The testing preceding release of a new variety should take into consideration research and development costs as well as technical superiority of the final variety. For seed-propagated varieties, it must be feasible to produce seed easily and economically. Preferably residual heterozygosity should not exceed 5%.

FURTHER EMBODIMENTS OF THE INVENTION

The seed of the soybean variety of the invention, the plant produced from the seed, the F1 progeny soybean plant produced from the crossing of the variety with any other soybean plant, F1 seed, and various parts of the F1 soybean plant are all intended to be within the scope of the invention. These plants and parts can be utilized for human food, livestock feed, as a raw material in industry, or as breeding material for development of other soybean varieties.

Certain changes and modifications such as single gene modifications and mutations, somoclonal variants, the creation of male sterile versions, creation of hybrids, variant individuals selected from large populations of the plants of the instant variety and the like may be practiced within the scope of the invention. These modifications may be created by methods such as backcrossing, transformation, creations of hybrids and the like.

Another such embodiment is the method of crossing soybean variety XB30W03 with another soybean plant, such as a different soybean variety, to form a first generation population of F1 hybrid plants. The population of first generation F1 hybrid plants produced by this method is also an embodiment of the invention. This first generation population of F1 plants will comprise an essentially complete set of the alleles of soybean variety XB30W03. One of ordinary skill in the art can utilize either breeder books or molecular methods to identify a particular F1 hybrid plant produced using soybean variety XB30W03, and any such individual plant is also encompassed by this invention. These embodiments also cover use of these methods with transgenic or backcross conversions of soybean variety XB30W03.

Another such embodiment of this invention is a method of using soybean variety XB30W03 in breeding that involves the repeated backcrossing to soybean variety XB30W03 any number of times. Using backcrossing methods, or even the tissue culture and transgenic methods described herein, the backcross conversion methods described herein, or other breeding methods known to one of ordinary skill in the art, one can develop individual plants, plant cells, and populations of plants that retain at least 25%, 30%, 35%, 40%, 45%, 50%, 55%, 60%, 65%, 70%, 75%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from soybean variety X830W03. The percentage of the genetics retained in the progeny may be measured by either pedigree analysis or through the use of genetic techniques such as molecular markers or electrophoresis. In using pedigree analysis one would determine that on average, 50% of the starting germplasm would be passed to the progeny variety after one cross to another variety, 25% after another cross to a different variety, and so on. Molecular markers could also be used to confirm and/or determine the pedigree of the progeny variety.

One method for producing a variety derived from soybean variety XB30W03 is as follows. One of ordinary skill in the art would obtain a seed from the cross between soybean variety XB30W03 and another variety of soybean, such as an elite variety. The F1 seed derived from this cross would be grown to form a homogeneous population. The F1 seed would contain essentially all of the alleles from variety XB30W03 and essentially all of the alleles from the other soybean variety. The F1 nuclear genome would be made-up of 50% variety XB30W03 and 50% of the other elite variety. The F1 seed would be grown and allowed to self, thereby forming F2 seed. On average the F2 seed would have derived 50% of its alleles from variety XB30W03 and 50% from the other soybean variety, but many individual plants from the population would have a greater percentage of their alleles derived from XB30W03 (Wang J. and R. Bernardo, 2000, Crop Sci. 40:659–665 and Bernardo, R. and A. L. Kahler, 2001, Theor. Appl. Genet 102:986–992). Molecular markers of XB30W03 could be used to select and retain those varieties with high similarity to XB30W03. The F2 seed would be grown and selection of plants would be made based on visual observation, markers and/or measurement of traits. The traits used for selection may be any XB30W03 trait described in this specification, including the soybean variety XB30W03 traits of Soybean Cyst Nematode resistance, Brown Stem Rot resistance, sudden death syndrome resistance, a substantial degree of glyphosate resistance, relative maturity group 3, sub-group 0, and particularly adapted to the Plains, Western, Mideast, Midwest, Heartland, and Eastern areas of the United States. The XB30W03 progeny plants that exhibit one or more of the desired XB30W03 traits, such as those listed above, would be selected and each plant would be harvested separately. This F3 seed from each plant would be grown in individual rows and allowed to self. Then selected rows or plants from the rows would be harvested individually. The selections would again be based on visual observation, markers and/or measurements for desirable traits of the plants, such as one or more of the desirable XB30W03 traits listed above. The process of growing and selection would be repeated any number of times until a XB30W03 progeny plant is obtained. The XB30W03 progeny plant would contain desirable traits derived from soybean plant XB30W03, some of which may not have been expressed by the other variety to which soybean variety XB30W03 was crossed and some of which may have been expressed by both soybean varieties but now would be at a level equal to or greater than the level expressed in soybean variety XB30W03. However, in each case the resulting progeny variety would benefit from the efforts of the inventor(s), and would not have existed but for the inventor(s) work in creating XB30W03. The XB30W03 progeny plants would have, on average, 50% of their genes derived from variety XB30W03, but many individual plants from the population would have a greater percentage of their alleles derived from XB30W03. This breeding cycle, of crossing and selfing, and optional selection, may be repeated to produce another population of XB30W03 progeny plants with, on average, 25% of their genes derived from variety XB30W03, but again, many individual plants from the population would have a greater percentage of their alleles derived from XB30W03. Another embodiment of the invention is a XB30W03 progeny plant that has received the desirable XB30W03 traits listed above through the use of XB30W03, which traits were not exhibited by other plants used in the breeding process.

The previous example can be modified in numerous ways, for instance selection may or may not occur at every selfing generation, selection may occur before or after the actual self-pollination process occurs, or individual selections may be made by harvesting individual pods, plants, rows or plots at any point during the breeding process described. In addition, double haploid breeding methods may be used at any step in the process. The population of plants produced at each and any cycle of breeding is also an embodiment of the invention, and on average each such population would predictably consist of plants containing approximately 50% of its genes from variety XB30W03 in the first breeding cycle, 25% of its genes from variety XB30W03 in the second breeding cycle, 12.5% of its genes from variety XB30W03 in the third breeding cycle and so on. However, in each case the use of XB30W03 provides a substantial benefit when linkage groups of XB30W03 are retained in the progeny varieties. Thus it provides a significant advantage to use XB30W03 as starting material to produce a variety that retains desired genetics or traits of XB30W03.

Another embodiment of this invention is the method of obtaining a substantially homozygous XB30W03 progeny plant by obtaining a seed from the cross of XB30W03 and another soybean plant and applying double haploid methods to the F1 seed or F1 plant or to any successive filial generation. Based on studies in maize and currently being conducted in soybean, such methods would decrease the number of generations required to produce a variety with similar genetics or characteristics to XB30W03. See Bernardo, R. and Kahler, A. L., Theor. Appl. Genet, 102:986–992 (2001).

A further embodiment of the invention is a backcross conversion of XB30W03. A backcross conversion occurs when DNA sequences are introduced through traditional (non-transformation) breeding techniques, such as back-crossing (Hallauer et at, 1988). DNA sequences, whether naturally occurring or transgenes, may be introduced using these traditional breeding techniques. The term backcross conversion is also referred to in the art as a single locus conversion. Reference is made to US 2002/0062506A1 for a detailed discussion of single locus conversions and traits that may be incorporated into XB30W03 through backcross conversion. Desired traits transferred through this process include, but are not limited to, nutritional enhancements, industrial enhancements, disease resistance, insect resistance, herbicide resistance and yield enhancements. The trait of interest is transferred from the donor parent to the recurrent parent, in this case, the soybean plant disclosed herein. Single gene traits may result from either the transfer of a dominant allele or a recessive allele. Selection of progeny containing the trait of interest is accomplished by direct selection for a trait associated with a dominant allele. Selection of progeny for a trait that is transferred via a recessive allele, requires growing and selfing the first backcross generation to determine which plants carry the recessive alleles. Recessive traits may require additional progeny testing in successive backcross generations to determine the presence of the gene of interest. Along with selection for the trait of interest, progeny are selected for the phenotype of the recurrent parent. It should be understood that occasionally additional polynucleotide sequences or genes are transferred along with the backcross conversion trait of interest. A progeny comprising at least 95%, 96%, 97%, 98%, 99%, 99.5% and 99.9% of the genes from the recurrent parent, the soybean variety disclosed herein, plus comprising the backcross conversion trait or traits of interest, would be considered to be a backcross conversion of soybean variety XB30W03. A progeny plant produced by using soybean variety XB30W03 at least 2, 3, 4, 5, 6, 7, or 8 times as a recurrent parent is within the scope of this invention.

As used herein, the term plant includes plant protoplasts, plant cell tissue cultures from which soybean plants can be regenerated, plant calli, plant clumps, and plant cells that are intact in plants or parts of plants, such as embryos, pollen, ovules, seed, flowers, pods, leaves, roots, root tips, anthers, and the like.

All plants produced using soybean variety XB30W03 as a parent are within the scope of this invention, including those developed from varieties derived from soybean variety XB30W03. Advantageously, the soybean variety could be used in crosses with other, different, soybean plants to produce first generation (F1) soybean hybrid seeds and plants with superior characteristics. The variety of the invention can also be used for transformation where exogenous genes are introduced and expressed by the variety of the invention. Genetic variants created either through traditional breeding methods using variety XB30W03 or through transformation of XB30W03 by any of a number of protocols known to those of skill in the art are intended to be within the scope of this invention.

Transformation of Soybean

The advent of new molecular biological techniques have allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes". Over the last fifteen to twenty years several methods for producing transgenic plants have been developed, and the present invention, in particular embodiments, also relates to transformed versions of the soybean variety XB30W03.

Numerous methods for plant transformation have been developed, including biological and physical, plant transformation protocols. See, for example, Miki et at., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

Various genetic elements can be introduced into the plant genome using transformation. These elements include but are not limited to genes; coding sequences; inducible, constitutive, and tissue specific promoters; enhancing sequences; and signal and targeting sequences. See U.S. Pat. No. 6,162,968, which is herein incorporated by reference.

A genetic trait which has been engineered into a particular soybean plant using transformation techniques, could be moved into another variety using traditional breeding techniques that are well known in the plant breeding arts. For example, a backcrossing approach could be used to move a transgene from a transformed soybean plant to an elite soybean variety and the resulting progeny would comprise a transgene. As used herein, "crossing" can refer to a simple X by Y cross, or the process of backcrossing, depending on the context. The term "cross" excludes the processes of selfing or sibbing.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981). In one embodiment, the biomass of interest is seed.

A genetic map can be generated, primarily via conventional RFLP, PCR, and SSR analysis, which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Through the transformation of soybean the expression of genes can be modulated to enhance disease resistance, insect resistance, herbicide resistance, agronomic traits as well as grain quality traits. Transformation can also be used to insert DNA sequences which control or help control male-sterility. DNA sequences native to soybean as well as non-native DNA sequences can be transformed into soybean and used to modulate levels of native or non-native proteins. Anti-sense technology, various promoters, targeting sequences, enhancing sequences, and other DNA sequences can be inserted into the soybean genome for the purpose of modulating the expression of proteins. Exemplary genes implicated in this regard include, but are not limited to, those categorized below.

Genes that Confer Resistance to Pests or Disease and that Encode (A) Plant disease resistance genes. Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains. See, for example Jones et al., Science 266:
789 (1994) (cloning of the tomato Cf-9 gene for resistance to *Cladosporium fulvum*); Martin et al., Science 262: 1432 (1993) (tomato Pto gene for resistance to *Pseudomonas sydngae* pv. tomato encodes a protein kinase); Mindrinos et al., Cell 78: 1089 (1994) (Arabidopsis RSP2 gene for resistance to *Pseudomonas syringae*).

(B) A gene conferring resistance to a pest, such as soybean cyst nematode. See e.g. PCT Application W096/30517; PCT Application W093/19181.

(C) A *Bacillus thuringiensis* protein, a derivative thereof or a synthetic polypeptide modeled thereon. See, for example, Geiser et al., Gene 48: 109 (1986), who disclose the cloning and nucleotide sequence of a Bt delta-endotoxin gene. Moreover, DNA molecules encoding delta-endotoxin genes can be purchased from American Type Culture Collection (Manassas, Va.), for example, under ATCC Accession Nos. 40098, 67136, 31995 and 31998. Other examples of *Bacillus thuringiensis* transgenes being genetically engineered are given in the following patents and hereby are incorporated by reference: U.S. Pat. Nos. 5,188,960: 5,689,052; 5,880,275; and WO 97/40162.

(D) A lectin. See, for example, the disclosure by Van Damme et al, *Plant Molec. Biol.* 24: 25 (1994), who disclose the nucleotide sequences of several *Clivia miniata* mannose-binding lectin genes.

(E) A vitamin-binding protein such as avidin. See PCT application US93/06487, the contents of which are hereby incorporated by reference. The application teaches the use of avidin and avidin homologues as larvicides against insect pests.

(F) An enzyme inhibitor, for example, a protease or proteinase inhibitor or an amylase inhibitor. See, for example, Abe et al., *J. Biol. Chem.* 262: 16793 (1987) (nucleotide sequence of rice cysteine proteinase inhibitor), Huub et at, *Plant Molec. Biol.* 21: 985 (1993) (nucleotide sequence of cDNA encoding tobacco proteinase inhibitor I), Sumitani et al., *Biosci. Biotech. Biochem.* 57: 1243 (1993) (nucleotide sequence of *Streptomyces nitrosporeus* alpha-amylase inhibitor) and U.S. Pat. No. 5,494,813 (Hepher and Atkinson, issued Feb. 27, 1996).

(G) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(H) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(I) An insect-specific venom produced in nature by a snake, a wasp, etc. For example, see Pang et al., Gene 116: 165 (1992), for disclosure of heterologous expression in plants of a gene coding for a scorpion insectotoxic peptide.

(J) An enzyme responsible for an hyperaccumulation of a monoterpene, a sesquiterpene, a steroid, hydroxamic acid, a phenylpropanoid derivative or another non-protein molecule with insecticidal activity.

(K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93102197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(L) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(M) A hydrophobic moment peptide. See PCT application W095/16776 (disclosure of peptide derivatives of Tachyplesin which inhibit fungal plant pathogens) and PCT application W095/18855 (teaches synthetic antimicrobial peptides that confer disease resistance), the respective contents of which are hereby incorporated by reference.

(N) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id. See also, Wang et al, *Molecular Breeding* 8: 119–127 (2001), Pathogen-Derived Resistance to Soybean Mosaic Virus in Soybean.

(P) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(Q) A virus-specific antibody. See, for example, Tavladoraki et al., Nature 366: 469 (1993), who show that transgenic plants expressing recombinant antibody genes are protected from virus attack.

(R) A developmental-arrestive protein produced in nature by a pathogen or a parasite. Thus, fungal endo alpha-1,4-D-polygalacturonases facilitate fungal colonization and plant nutrient release by solubilizing plant cell wall homoalpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(S) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(T) Genes involved in the Systemic Acquired Resistance (SAR) Response and/or the pathogenesis related genes. Briggs, S., Current Biology, 5(2) (1995).

(U) Antifungal genes (Cornelissen and Melchers, Pl. Physiol. 101:709–712, (1993) and Parijs et al., Planta 183:258–264, (1991) and Bushnell et al., Can. J. of Plant Path. 20(2):137–149 (1998).

(V) Genes that confer resistance to Phytophthora Root Rot, such as the Rps 1, Rps 1-a, Rps 1-b, Rps 1-c, Rps 1-d, Rps 1-e, Rps 1-k, Rps 2, Rps 3-a, Rps 3b, Rps 3-c, Rps 4, Rps 5, Rps 6, Rps 7 and other Rps genes. See, for example, Shoemaker et al, Phytophthora Root Rot Resistance Gene Mapping in Soybean, Plant Genome IV Conference, San Diego, Calif. (1995).

(W) Genes that confer resistance to Brown Stem Rot, such as described in U.S. Pat. No. 5,689,035 and incorporated by reference for this purpose.

Genes that Confer Resistance to a Herbicide, for Example (A) A herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl.Genet.* 80: 449 (1990), respectively. See also, U.S Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference in their entireties for all purposes.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and *Streptomyces hygroscopicus* phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. describes genes encoding EPSPS enzymes. See also U.S. Pat. Nos. 6,248,876 B1;6,040,497; 5,804,425; 5,633,435; 5,145,783; 4,971,908; 5,312,910; 5,188,642; 4,940,835; 5.866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103;WO97/04114; WO 00/66746; WO 01/66704; WO 00/66748 and WO 00/66747, which are incorporated herein by reference in their entireties for all purposes. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entireties for all purposes. In addition glyphosate resistance can be imparted to plants by the over expression of genes encoding glyphosate N-acetyltransferase. See, for example, U.S. Application Serial Nos. 60/244,385; 60/377,175 and 60/377,719.

A DNA molecule encoding a mutant aroA gene can be obtained under ATCC Accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference in their entireties for all purposes. Exemplary of genes conferring resistance to phenoxy propionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+genes) and a benzonitrile (nitrilase gene). Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285:173 (1992).

(D) Acetohydroxy acid synthase, which has been found to make plants that express this enzyme resistant to multiple types of herbicides, has been introduced into a variety of plants (see, e.g., Hattori et al. (1995) *Mol Gen Genet* 246:419). Other genes that confer tolerance to herbicides include: a gene encoding a chimeric protein of rat cytochrome P4507A1 and yeast NADPH-cytochrome P450 oxidoreductase (Shiota et al. (1994) *Plant Physiol Plant Physiol* 106:17), genes for glutathione reductase and superoxide dismutase (Aono et al. (1995) *Plant Cell Physiol* 36:1687, and genes for various phosphotransferases (Datta et al. (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825, which are incorporated herein by reference in their entireties for all purposes.

Genes that Confer or Contribute to a Grain Trait, such As (A) Modified fatty acid metabolism, for example, by transforming a plant with an antisense gene of stearoyl-ACP desaturase to increase stearic acid content of the plant. See Knultzon et al., *Proc. Nat'l. Acad. Sci. USA* 89: 2624 (1992).

(B) Decreased phytate content (1) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(2) A gene could be introduced that reduces phytate content. In maize, this, for example, could be accomplished, by cloning and then reintroducing DNA associated with the single allele which is responsible for maize mutants characterized by low levels of phytic acid. See Raboy et al., *Maydica* 35: 383 (1990).

(C) Modified carbohydrate composition effected, for example, by transforming plants with a gene coding for an enzyme that alters the branching pattern of starch. See Shiroza et al., *J. Bacteriol.* 170: 810 (1988) (nucleotide sequence of *Streptococcus mutans* fructosyltransferase gene), Steinmetz et al., *Mol. Gen. Genet.* 200: 220 (1985) (nucleotide sequence of *Bacillus subtilis* levansucrase gene), Pen et al., *Bio/Technology* 10: 292 (1992) (production of transgenic plants that express *Bacillus licheniformis* alpha-amylase), Elliot et al., *Plant Molec. Biol.* 21: 515 (1993) (nucleotide sequences of tomato invertase genes), Søgaard et al., *J. Biol. Chem.* 268: 22480 (1993) (site-directed mutagenesis of barley alpha-amylase gene), and Fisher et at,, *Plant Physiol.* 102: 1045 (1993) (maize endosperm starch branching enzyme II). Also, genes that encode for galactinol synthase, such as in U.S. Pat. Nos. 5,648,210 and 5,773,699, or genes that encode for raffinose synthetic enzymes, such as U.S. Pat. No. 6,166,292, EP0994186 and WO0177306.

(D) Elevated oleic acid via FAD-2 gene modification and/or decreased linolenic acid via FAD-3 gene modification (see U.S. Pat. Nos. 6,063,947; 6,323,392; and WO 93/11245).

4. Genes that Control Male-sterility (A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the bamase and the barstar gene (Paul et al. Plant Mol. Biol. 19:611–622, 1992).

Numerous methods for plant transformation have been developed, including biological and physical, plant transformation protocols. See, for example, Miki et at., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119. See also, U.S. Pat. No. 5,563,055, (Townsend and Thomas), issued Oct. 8, 1996; U.S. Pat. No. 5,015,580 (Christou, et al), issued May 14, 1991; U.S. Pat. No. 5,322,783 (Tomes, et al.), issued Jun. 21, 1994. Two methods that can be utilized are Agromediated transformation and direct gene transfer. See U.S. Pat. No. 6,162,968, which is herein incorporated by reference.

This invention also is directed to methods for producing a soybean plant by crossing a first parent soybean plant with a second parent soybean plant wherein the first or second parent soybean plant is a soybean plant of the variety XB30W03. Further, both first and second parent soybean plants can come from the soybean variety XB30W03. Still further, this invention also is directed to methods for producing XB30W03-derived soybean plant by crossing soybean variety XB30W03 with a soybean plant and growing the progeny seed, and repeating the crossing and growing steps with the XB30W03-derived soybean plant from 1 to 2 times, 1 to 3 times, 1 to 4 times, or 1 to 5 times. Thus, any such methods using soybean variety XB30W03 are part of this invention: selfing, backcrosses, hybrid production, crosses to populations, and the like. All plants produced using soybean variety XB30W03 as a parent are within the scope of this invention, including plants derived from soybean variety XB30W03. This includes varieties essentially derived from variety XB30W03 with the term "essentially derived variety" having the meaning ascribed to such term in 7 U.S.C. §2104(a)(3) of the Plant Variety Protection Act, which definition is hereby incorporated by reference. The invention also includes progeny plants and parts thereof with at least one ancestor that is XB30W03, and more specifically, where the pedigree of the progeny includes 1, 2, 3, 4, and/or 5 or less cross-pollinations to a soybean plant other than XB30W03 or a plant that has XB30W03 as a progenitor. All breeders of ordinary skill in the art maintain pedigree records of their breeding programs. These pedigree records contain a detailed description of the breeding process, including a listing of all parental varieties used in the breeding process and information on how such variety was used. Thus, a breeder would know if XB30W03 were used in the development of a progeny variety, and would also know how many crosses to a plant or variety other than XB30W03 or a plant or variety with XB30W03 as a progenitor were made in the development of any progeny variety. The soybean variety may also be used in crosses with other, different soybean plant to produce first generation (F1) soybean seeds and plants with superior characteristics. Specific methods and products produced using soybean variety XB30W03 in plant breeding are encompassed within the scope of the invention listed above.

The following describes breeding methods that may be used with variety XB30W03 in the development of further soybean plants. One such embodiment is a method for developing a XB30W03 progeny soybean plant in a soybean plant breeding program comprising: obtaining the soybean plant, or its parts, or variety XB30W03 utilizing said plant or plant parts as a source of breeding material; and selecting a XB30W03 progeny plant with molecular markers in common with XB30W03 and/or with morphological and/or physiological characteristics selected from the characteristics listed in Tables 1 or 2. Breeding steps that may be used in the soybean plant breeding program include pedigree breeding, backcrossing, mutation breeding, and recurrent selection. In conjunction with these steps, techniques such as restriction fragment polymorphism enhanced selection, genetic marker enhanced selection (for example SSR markers), and the making of double haploids may be utilized.

Another method involves producing a population of variety XB30W03 progeny soybean plants, comprising crossing variety XB30W03 with another soybean plant, thereby producing a population of soybean plants, which, on average, derive 50% of their alleles from variety XB30W03. A plant of this population may be selected and repeatedly selfed or sibbed, with a soybean variety resulting from these successive filial generations. One embodiment of this invention is the soybean variety produced by this method and that has obtained at least 50% of its alleles from variety XB30W03.

Field crops are bred through techniques that take advantage of the plant's method of pollination. According to the invention, soybean variety XB30W03 may be crossed with self pollinated, sib-pollinated, or cross pollinated to create a pedigree soybean plant. A plant is self-pollinated if pollen from one flower is transferred to the same or another flower of the same plant. A plant is sib-pollinated when individuals within the same family or variety are used for pollination. A plant is cross-pollinated if the pollen comes from a flower on a different plant from a different family or variety.

The terms "cross-pollination" and "out-cross" as used herein do not include self-pollination or sib-pollination. Soybean plants (Glycine max), are recognized to be naturally self-pollinated plants which, while capable of undergoing cross-pollination, rarely do so in nature. Insects are reported by some researchers to carry pollen from one soybean plant to another and it generally is estimated that less than one percent of soybean seed formed in an open planting can be traced to cross-pollination, i.e. less than one percent of soybean seed formed in an open planting is capable of producing F1 hybrid soybean plants, See Jaycox, "Ecological Relationships between Honey Bees and Soybeans," appearing in the American Bee Journal Vol. 110(8): 306–307 (August 1970). Thus intervention for control of pollination is critical to establishment of superior varieties.

A cross between two different homozygous varieties produces a uniform population of hybrid plants that may be heterozygous for many gene loci. A cross of two plants that differ at a number of gene loci will produce a population of hybrid plants that differ genetically and will not be uniform. Regardless of parentage, plants that have been self-pollinated and selected for type for many generations become homozygous at almost all gene loci and produce a uniform population of true breeding progeny.

Soybean variety XB30W03 can be bred by both self-pollination and cross-pollination techniques. Soybean plant breeding programs combine the genetic backgrounds from two or more lines, varieties or various other germplasm sources into breeding populations from which new lines or varieties are developed by selfing and selection of desired phenotypes. Plant breeding and variety, line or hybrid development, as practiced in a soybean plant breeding program developing significant genetic advancement, are expensive and time consuming processes Choice of breeding or selection method used with soybean variety XB30W03 depends on the mode of plant reproduction, the heritability of the trait(s) being improved, and the type of variety used commercially (e.g., F1 hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. The complexity of inheritance influences choice of the breeding method. In general breeding with the soybean variety of the invention starts with the crossing of two genotypes, each of which may have one or more desirable characteristics that is lacking in the other or which complements the other. If the two original parents do not provide all the desired characteristics, other sources can be included by making more crosses. In each successive filial generation, superior plants are selected and self-pollinated which increases the homozygosity of the varieties. Typically in a breeding program five or more successive filial generations of selection and selfing are practiced: F1→F2; F2→F3; F3→F4; F4→F5, etc. After a sufficient amount of inbreeding, successive filial generation will serve to increase seed of the developed variety. Preferably, a developed variety comprises homozygous allele at about 95% or more of its loci.

Pedigree breeding may be used for the development of XB30W03 soybean progeny plants. Two parents that possess favorable, complementary traits are crossed to produce an F1. An F2 population is produced by selfing one or several F1's or by intercrossing two F1's (sib mating). Selection of the best individuals may begin in the F2 population; then, beginning in the F3, the best individuals in the successive filial generations are selected. Replicated testing of families can begin in the F4 generation to improve the effectiveness of selection for traits with low heritability. At an advanced stage of inbreeding (i.e., F6 and F7), the best varieties or mixtures of phenotypically similar varieties are tested for potential release as new varieties.

Backcross breeding has been used to transfer genes for qualitative traits, which are highly heritable traits, from a donor parent into a desirable homozygous variety that is utilized as the recurrent parent. For purposes of the invention, soybean variety XB30W03 may be used as either the donor or recurrent parent for backcross breeding. The source of the traits to be transferred is called the donor parent. After the initial cross, individuals possessing the desired trait or traits of the donor parent are selected and then repeatedly crossed (backcrossed) with the recurrent parent. The resulting backcross conversion plant has essentially the same traits as the recurrent parent (e.g., variety) other than the desirable trait or traits transferred from the donor parent. This approach has been used extensively for breeding disease resistant varieties.

Each soybean breeding program should include a periodic, objective evaluation of the efficiency of the breeding procedure. Evaluation criteria vary depending on the goal and objectives, but should include gain from selection per year based on comparisons to an appropriate standard, overall value of the advanced breeding varieties, and number of successful varieties produced per unit of input (e.g., per year, per dollar expended, etc.).

Various recurrent selection techniques may be used to improve quantitatively inherited traits controlled by numerous genes. The use of recurrent selection in self-pollinating crops depends on the ease of pollination and the number of hybrid offspring from each successful cross.

Mass selection and recurrent selection may be used to improve populations of either self- or cross-pollinated crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which varieties are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, soybean breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Molecular markers which includes markers identified through the use of techniques such as such Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs) may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. For example, molecular markers are often used in soybean breeding for selection of the trait of resistance to soybean cyst nematode, See, U.S. Pat. No. 6,162,967. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection. Molecular markers may also be used to identify and exclude certain sources of germplasm as parental varieties or ancestors of a plant by providing a means of tracking genetic profiles through crosses as discussed more fully hereinafter.

Descriptions of other breeding methods that are commonly used for different traits and crops can be found in one of several reference books (e.g., Allard, *Principles of Plant Breeding,* 1960; Simmonds, *Principles of Crop Improvement,* 1979; Sneep et al., 1979; Fehr, "Breeding Methods for Cultivar Development", Chapter 7, *Soybean Improvement, Production and Uses,* $2^{nd}$ ed., Wilcox editor, 1987).

Promising advanced breeding varieties are thoroughly tested and compared to appropriate standards in environments representative of the commercial target area(s). The best varieties are candidates for new commercial varieties; those still deficient in a few traits may be used as parents to produce new populations for further selection.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. Generally a single observation is inconclusive, so replicated observations are required to provide a better estimate of its genetic worth.

Thus, even if the entire genotypes of the parents of the breeding cross were characterized and a desired genotype known, only a few if any individuals having the desired genotype may be found in a large segregating F2 population. It would be very unlikely that a breeder of ordinary skill in the art would be able to recreate the same variety twice from the very same original parents as the breeder is unable to direct how the genomes combine or how they will interact with the environmental conditions. This unpredictability results in the expenditure of large amounts of research resources in the development of a superior new soybean variety. Breeders use various methods to help determine which plants should be selected from the segregating populations and ultimately which varieties will be used for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which varieties are significantly better or different for one or more traits of interest. Experimental design methods are used to assess error so that differences between two varieties can be more accurately determined. Statistical analysis includes the calculation of mean values, determination of the statistical significance of the sources of variation, and the calculation of the appropriate variance components. Either a five or a one percent significance levels is customarily used to determine whether a difference that occurs for a given trait is real or due to the environment or experimental error.

One of ordinary skill in the art of plant breeding would know how to evaluate the traits of two plant varieties to determine if there is no significant difference between the two traits expressed by those varieties. For example, see Fehr, Walt, Principles of Cultivar Development, p. 261–286 (1987) which is incorporated herein by reference. Thus the invention includes soybean variety XB30W03 progeny soybean plants comprising a combination of at least two XB30W03 traits selected from the group consisting of those listed in Tables 1 and 2 or the XB30W03 combination of traits listed in the Summary of the Invention, so that said progeny soybean plant is not significantly different for said traits than soybean variety XB30W03 when grown in the same environment. Using techniques described herein, molecular markers may be used to identify said progeny plant as an XB30W03 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme weather conditions.

Progeny of variety XB30W03 may also be characterized through their filial relationship with soybean variety XB30W03, as, for example, being within certain number of breeding crosses of soybean variety XB30W03. A breeding cross is a cross made to introduce new genetics into the progeny, and is distinguished from a cross, such as a self or a sib cross, made to select among existing genetic alleles. The lower the number of breeding crosses in the pedigree, the closer the relationship between soybean variety XB30W03 and its progeny. For example, progeny produced by the methods described herein may be within 1, 2, 3, 4 or 5 breeding crosses of soybean variety XB30W03.

A soybean variety needs to be homogeneous, substantially homozygous and reproducible to be useful as a commercial variety. There are many analytical methods available to determine the homozygotic stability, phenotypic stability, and identity of these varieties.

The oldest and most traditional method of analysis is the observation of phenotypic traits. The data is usually collected in field experiments over the life of the soybean plants to be examined. Phenotypic characteristics most often observed are for traits associated with seed yield, seed protein and oil content, lodging resistance, disease resistance, maturity, plant height, shattering resistance, etc.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Isozyme Electrophoresis and RFLPs have been widely used to determine genetic composition. Shoemaker and Olsen, ((1993) Molecular Linkage Map of Soybean (*Glycine max* L. Merr.). p. 6.131–6.138. In S. J. O'Brien (ed.) Genetic Maps: Locus Maps of Complex Genomes. Cold Spring Harbor Laboratory Press. Cold Spring Harbor, N.Y.), developed a molecular genetic linkage map that consisted of 25 linkage groups with about 365 RFLP, 11 RAPD (random amplified polymorphic DNA), three classical markers, and four isozyme loci. See also, Shoemaker R. C. 1994 RFLP Map of Soybean. P. 299–309 In R. L. Phillips and I. K. Vasil (ed.) DNA-based markers in plants. Kluwer Academic Press Dordrecht, the Netherlands.

SSR technology is currently the most efficient and practical marker technology; more marker loci can be routinely used and more alleles per marker locus can be found using SSRs in comparison to RFLPs. For example Diwan and Cregan, described a highly polymorphic microsatellite loci in Soybean with as many as 26 alleles. (Diwan, N., and P. B. Cregan 1997 Automated sizing of fluorescent-labeled simple sequence repeat (SSR) markers to assay genetic variation in Soybean Theor. Appl. Genet. 95:220–225.) Single Nucleotide Polymorphisms may also be used to identify the unique genetic composition of the invention and progeny varieties retaining that unique genetic composition. Various molecular marker techniques may be used in combination to enhance overall resolution.

Soybean DNA molecular marker linkage maps have been rapidly constructed and widely implemented in genetic studies. One such study is described in Cregan et. al, "An Integrated Genetic Linkage Map of the Soybean Genome" Crop Science 39:1464–1490 (1999). Sequences and PCR conditions of SSR Loci in Soybean as well as the most current genetic map may be located at the world wide web soybase.agron.iastate.edu or at soybase.ncgr.org the disclosures of which are incorporated herein by reference.

Mutation breeding is another method of introducing new traits into soybean variety XB30W03. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principals of Cultivar Development" Fehr, 1993 Macmillan Publishing Company the disclosure of which is incorporated herein by reference. The production of double haploids can also be used for the development of homozygous varieties in the breeding program. Double haploids are produced by the doubling of a set of chromosomes (1 N) from a heterozygous plant to produce a completely homozygous individual. For example. See Wan et al., "Efficient Production of Doubled Haploid Plants Through Colchicine Treatment of Anther-Derived Maize callus" Theoretical and Applied genetics, 77:889–892, 1989. This can be advantageous because the process omits the generations of selfing needed to obtain a homozygous plant from a heterozygous source.

This invention is also directed to the use of variety XB30W03 in tissue culture. Tissue culture of various tissues of soybeans and regeneration of plants therefrom is well known and widely published. For example, reference may be had to Komatsuda, T. et al., "Genotype X Sucrose Interactions for Somatic Embryogenesis in Soybean," Crop Sci. 31:333–337 (1991); Stephens, P. A. et al., "Agronomic Evaluation of Tissue-Culture-Derived Soybean Plants," Theor. Appl. Genet (1991) 82:633–635; Komatsuda, T. et al., "Maturation and Germination of Somatic Embryos as Affected by Sucrose and Plant Growth Regulators in Soybeans *Glycine gracis* Skvortz and *Glycine max* (L.) Merr.," Plant Cell, Tissue and Organ Culture, 28:103–113 (1992); Dhir, S. et al., "Regeneration of Fertile Plants from Protoplasts of Soybean (*Glycine max* L. Merr.): Genotypic Differences in Culture Response," Plant Cell Reports (1992) 11:285–289; Pandey, P. et al., "Plant Regeneration from Leaf and Hypocotyl Explants of *Glycine wightii* (W. and A.) VERDC. *var. longicauda*," Japan J. Breed. 42:1–5 (1992); and Shetty, K., et al., "Stimulation of in Vitro Shoot Organogenesis in *Glycine max* (Merrill.) by Allantoin and Amides," Plant Science 81:(1992) 245–251; as well as U.S. Pat. No. 5,024,944, issued Jun. 18, 1991 to Collins et al. and U.S. Pat. No. 5,008,200, issued Apr. 16, 1991 to Ranch et al., the disclosures of which are hereby incorporated herein in their entirety by reference. Thus, another aspect of this invention is to provide cells which upon growth and differentiation produce soybean plants having the physiological and morphological characteristics of soybean variety XB30W03.

DEPOSITS

Applicant(s) have made a deposit of at least 2500 seeds of Soybean Variety XB30W03 with the American Type Culture Collection (ATCC), Manassas, Va. 20110 USA, ATCC Deposit No. PTA-5772. The seeds deposited with the ATCC on Jan. 15, 2004 were taken from the deposit maintained by Pioneer Hi-Bred International, Inc., 800 Capital Square, 400 Locust Street, Des Moines, Iowa 50309–2340 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will make the deposit available to the public pursuant to 37 CFR 1.808. This deposit of Soybean Variety XB30W03 will be maintained in the ATCC depository, which is a public depository, for a period of 30 years, or 5 years after the most recent request or for the enforceable life of the patent, whichever is longer, and will be replaced if it becomes nonviable during that period. Additionally, Applicant(s) have or will satisfy all the requirements of 37 C.F.R. §§1.801–1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or under the Plant Variety Protection Act (7 USC 2321 et seq.) U.S. Plant Variety Protection of Soybean Variety XB30W03 has been applied for under Application No- 200400081.

All publications, patents and patent applications mentioned in the specification are indicative of the level of those skilled in the art to which this invention pertains. All such publications, patents and patent applications are incorporated by reference herein to the same extent as if each was specifically and individually indicated to be incorporated by reference herein.

The foregoing invention has been described in detail by way of illustration and example for purposes of clarity and understanding. However, it will be obvious that certain changes and modifications such as backcross conversions, mutations, somoclonal variants, variant individuals selected from large populations of the plants of the instant variety and the like may be practiced within the scope of the invention.

What is claimed is:

1. A soybean seed of soybean variety XB30W03, representative seed of said soybean variety XB30W03 having been deposited under ATCC Accession No: PTA-5772.

2. A soybean plant, or a part thereof, produced by growing the seed of claim 1.

3. The soybean plant or a part thereof of claim 2, wherein said part is pollen.

4. The soybean plant or a part thereof of claim 2, wherein said part is an ovule.

5. A tissue culture of protoplasts or regenerable cells from the plant of claim 2.

6. The tissue culture according to claim 5, the cells or protoplasts of the tissue culture are obtained from a plant tissues selected from the group consisting of: leaf, pollen, cotyledon, hypocotyl, embryos, root, pod, flower, shoot and stem.

7. A soybean plant regenerated from the tissue culture of claim 5, wherein the regenerated plant has all the morphological and physiological charactristics of soybean variety XB30W03, representative seed of said soybean variety XB30W03 having been deposited under ATCC Accession No: PTA-5772.

8. A method for producing a progeny soybean plant comprising crossing the plant of claim 2 with a second soybean plant, harvesting the resultant soybean seed, and a growing a progeny soybean plant.

* * * * *

UNITED STATES PATENT AND TRADEMARK OFFICE
CERTIFICATE OF CORRECTION

PATENT NO. : 6,809,236 B1
DATED : October 26, 2004
INVENTOR(S) : Stephens et al.

It is certified that error appears in the above-identified patent and that said Letters Patent is hereby corrected as shown below:

Column 38,
Line 17, delete the word "a" between the word "from" and "plant"
Line 29, delete the "a" after the word "and"

Signed and Sealed this

Fourth Day of January, 2005

JON W. DUDAS
*Director of the United States Patent and Trademark Office*